United States Patent [19]

Carpenter et al.

[11] Patent Number: 5,342,339

[45] Date of Patent: Aug. 30, 1994

[54] PRESSURE-SENSITIVE ADHESIVE CLOSURE FOR DISPOSABLE DIAPER

[75] Inventors: Theresa L. Carpenter; Alan J. Sipinen; Stephen W. Bany, all of St. Paul, Minn.

[73] Assignee: Minnesota Mining and Manufacturing Company, St. Paul, Minn.

[21] Appl. No.: 702,447

[22] Filed: May 16, 1991

Related U.S. Application Data

[60] Continuation of Ser. No. 390,284, Aug. 7, 1989, abandoned, which is a division of Ser. No. 118,319, Nov. 6, 1987, Pat. No. 4,681,635.

[51] Int. Cl.$^5$ .................. A61F 13/15; A61F 13/20
[52] U.S. Cl. .................. 604/385.1; 604/389
[58] Field of Search ............ 604/366, 389, 390, 385.1; 428/40

[56] References Cited

U.S. PATENT DOCUMENTS

| | | | |
|---|---|---|---|
| 3,271,229 | 9/1966 | Grabovez | 428/141 |
| 3,535,153 | 10/1970 | Korpman | 428/355 |
| 3,787,531 | 1/1974 | Dahlquist et al. | 428/355 |
| 3,867,940 | 2/1975 | Mesek et al. | 604/366 |
| 4,023,570 | 5/1977 | Chinai et al. | 604/390 X |
| 4,163,077 | 7/1979 | Antonsen et al. | 428/355 |
| 4,237,889 | 12/1980 | Gobran | 604/389 |
| 4,376,147 | 3/1983 | Byrne et al. | 428/167 |
| 4,397,905 | 8/1983 | Dettmer et al. | 428/180 |
| 4,424,244 | 1/1984 | Puskadi | 428/40 |
| 4,436,520 | 3/1984 | Lipko et al. | 604/385 |
| 4,460,364 | 7/1984 | Chen et al. | 604/389 |
| 4,526,577 | 7/1985 | Schmidt et al. | 604/366 |
| 4,540,415 | 9/1985 | Korpman | 604/389 |
| 4,546,029 | 10/1985 | Cancio et al. | 428/141 |
| 4,575,649 | 4/1986 | Pazdernik | 604/389 |
| 4,587,152 | 5/1986 | Gleichenhagen et al. | 428/195 |
| 4,655,761 | 4/1987 | Grube et al. | 604/389 |
| 4,704,110 | 11/1987 | Raykovitz et al. | 604/366 |
| 4,710,190 | 12/1987 | Wood | 604/389 |
| 4,759,754 | 7/1988 | Korpman | 604/389 |
| 4,861,635 | 8/1989 | Carpenter et al. | 428/40 |

FOREIGN PATENT DOCUMENTS

| | | | |
|---|---|---|---|
| 0563480 | 6/1960 | Belgium | 604/389 |
| 2129689 | 5/1984 | United Kingdom | 604/389 |

*Primary Examiner*—C. Fred Rosenbaum
*Assistant Examiner*—Vanitha Alexander
*Attorney, Agent, or Firm*—Gary L. Griswold; Walter N. Kirn; Roger R. Tamte

[57] ABSTRACT

A pressure-sensitive adhesive closure for a disposable diaper can exhibit high peel resistance both at low and high speeds while its peelability at high speeds is not excessively shocky when it employs a pressure-sensitive adhesive of a certain rheology and it has, covering the fastening area, a polyolefin layer having microtopographical features as in FIGS. 1-6 of the drawing. As seen in FIGS. 1-6, suitable microtopographical features are provided by a large number of closely spaced asperities at least two micrometers in height that have a jagged appearance at 500×. A pressure-sensitive adhesive of suitable rheology can be provided by a blend of an AB block copolymer, such as a copolymer of styrene and either isoprene or butadiene, and tackifying resin, preferably a mixture of liquid and solid tackifying resins.

5 Claims, 10 Drawing Sheets

PRESSURE-SENSITIVE ADHESIVE CLOSURE FOR DISPOSABLE DIAPER

This is a continuation of application Ser. No. 07/390,284 filed Aug. 7, 1989, now abandoned which is a divisional of application Ser. No. 07/118,319 filed Nov. 6, 1987, now U.S. Pat. No. 4,681,635.

BACKGROUND ART

1. Field of the Invention

The invention concerns disposable garments such as diapers for infants and for incontinent adults, more specifically a pressure-sensitive adhesive closure that can be peeled open and reclosed. The invention particularly concerns improvements in the closure.

2. Description of the Related Art

Many disposable diapers have a reinforced fastening area (sometimes called a "target area") to which a pressure-sensitive adhesive fastening tape (sometimes called a "closure tab") is pressed and adhered to fasten the diaper around an infant or other person wearing the diaper. Whether or not the fastening area is reinforced, the fastening tape should remain securely in place while the diaper is being worn and should be cleanly peelable from the fastening area and capable of being securely reattached. Although forces which may cause the fastening tape to become loose during use of the diaper generally occur at low speeds, e.g., up to about 30 cm/min., a person who readjusts or removes a diaper may judge the closure to be of poor quality if the fastening tape peels off too easily or in an excessively shocky manner when removed quickly, e.g., at about 500 to 1250 cm/min. We are not aware of any report in the prior art of a pressure-sensitive adhesive closure for a diaper that would provide high peel resistance both at low and high speeds without being excessively shocky at high speeds, nor do we believe that any such diaper closure has been sold or offered for sale.

U.S. Pat. No. 4,376,147 (Byrne et al.) concerns an embossed thermoplastic polyolefin film which has a matte finish that "is extremely low in gloss even on both sides and tape adhesion values are achieved which render the film particularly useful for fabrication into . . . disposable diapers where such adhesion values are needed" (col. 2, lines 54–59). The adhesive which provides "such adhesion values" is not disclosed, and the only adhesion values given are at col. 5, line 38 without indicating their significance.

U.S. Pat. No. 4,546,029 (Cancio et al.), like the Byrne patent, concerns an embossed thermoplastic polyolefin film simulating a matte or dull finish, but its embossing is asymmetric as opposed to the symmetry of the Byrne embossing, thus providing "a totally different visual appearance" (col. 3, lines 9–10). Unlike the Byrne patent, the Cancio patent explains the reported tape adhesion values. Its Table (col. 7) gives such values for the asymmetrically embossed film, showing improvement versus the Byrne film, but as in the Byrne patent, there is no disclosure of the adhesive tape used in making those measurements.

U.S. Pat. No. 4,436,520 (Lipko et al.) says that the exposed surface of a film used as a diaper back sheet typically is embossed to reduce gloss, but that "the embossing materially reduces the adhesion of the embossed surface for the closure tabs so that the diaper is no longer secure in its use on the infant" (col. 1, lines 19–22). The Lipko patent concerns the discovery "in embossed films of polyethylene having a (45°) gloss of no greater than 8, the adhesion of the embossed surface is markedly enhanced when said surface has a mean value of maximum profile height of less than 150 and maximum peak to valley height of less than 230″ (col. 1, lines 35–40). The profile measurements are made with a "Surtronic" 3 apparatus sold by Taylor-Hobson. The adhesive tape used for making the reported tape adhesion values is not disclosed.

U.S. Pat. No. 4,237,889 (Gobran) concerns an improved closure tab or fastening tape for a disposable diaper. The improvement is in the tape backing which is a substantially untensilized crystalline polypropylene or linear polyethylene foil having one smooth face and one textured face. There is no disclosure of a pressure-sensitive adhesive to be used on the fastening tape.

European Patent Application 82110676.4 (Raphael et al.), published Aug. 6, 1983, concerns a diaper having an impermeable outer sheet which has been calendered to provide a matte appearance. This is reinforced at the fastening area with an impermeable sheet which may be polypropylene that is perfectly smooth as opposed to the matte surface of the underlying sheet. The smoothness is said to improve adhesion by the fastening tape.

German Patent Application P 33 38 201.8 (Widlund), laid open Apr. 26, 1984, indicates that a disposable diaper typically has an outer polyethylene layer to which a pressure-sensitive adhesive fastening tape will not adhere well because the surface of the polyethylene layer is not sufficiently smooth. This problem is avoided by applying to the fastening area of the diaper one or several plastic strips which are selected to provide good adhesion by the fastening tape and preferably are smooth and flat.

SUMMARY OF THE INVENTION

The invention provides for the first time a pressure-sensitive adhesive closure for a disposable article such as a diaper that affords high peel resistance at both low and high speeds while being smoothly peelable at high speeds. By "high peel resistance" is meant that the closure has a "Mean Peel Force" as described below of at least 175 N/m. By "low speed" is meant 12 inches (30 cm) per minute, and by "high speed" is meant at least 500 inches (1250 cm) per minute. Extensive testing indicates that the peelability of a pressure-sensitive adhesive closure is not excessively shocky at high speeds whenever its Mean Peel Force at 1250 cm/min. is at least 80% of its Mean Peel Force at 30 cm/min. At less than 80%, excessively "shocky" peel has been encountered. Preferably, the instantaneous peel force at 1250 cm/min. stays substantially within 20% of the Mean Peel Force. The pressure-sensitive adhesive should afford good resistance to shear, i.e., a Shear Adhesion Value (as described below) of at least 150 minutes. Furthermore, in order to permit the pressure-sensitive adhesive fastening tape to be shipped in commerce, the adhesive should not ooze from long rolls (e.g., lengths of about 500 m or more), and it should be possible to unwind the rolls without offsetting of adhesive after long and possibly adverse storage conditions.

This desirable combination of properties is achieved by both a) using a certain class of pressure-sensitive adhesives in the fastening tape and b) employing at the fastening area a polyolefin layer having certain microtopographical features. More specifically, the pressure-sensitive adhesive of the fastening tape comprises a blend of 1) an AB block copolymer wherein A comprises vinylarene, B comprises a polymer of at least one monomer selected from conjugated dienes and alkenes, and A comprises from 8 to 50 weight percent of the block copolymer, and 2) tackifying resin (preferably a blend of liquid and solid tackifying resins), the AB copolymer comprising from 20 to 60 weight percent of total AB copolymer plus tackifier and the B phase of the blend having a composite Tg of from 250° to 275° K., and the surface of the polyolefin layer at the fastening area has a large number of closely spaced asperities that have a jagged appearance when viewed at a magnification of about 500× and are at least two micrometers in height. By "jagged" is meant a sharply uneven surface. As much as half of the total area of the surface of the polyolefin at the fastening area can have a smooth or rounded appearance at 500×.

DETAILED DESCRIPTION

For a full evaluation of the nature of the asperities, the fastening area should also be examined at lesser and greater magnifications, e.g., at 100× and 1500×. Examination at 100× should indicate whether the area at 500× is truly representative, and examination at 1500× can better reveal the true nature of individual asperities.

In an intensive effort to ascertain whether microtopographical measurements could be made of polyolefin surfaces to show which of those surfaces would be useful in the present invention and which would not, various instruments have been used. One such instrument is the "Surtronic" 3 profilometer mentioned above in the discussion of the Lipko patent. Another is the "Perthometer" profilometer made by Perthen GmbH of Gottingen, West Germany, which is a more sophisticated instrument than the "Surtronic" 3 and, accordingly, provides measurements which have been found to be more meaningful than those obtained with the "Surtronic" 3. Optical microtopographical measurements have also been made, as well as gloss readings. However, no combination of microtopographical measurements has been found which can provide a reliable prediction as to whether a new polyolefin surface would or would not provide the objectives of the invention. In contrast, photomicrographs of the polyolefin surfaces permit one skilled in the art to predict with reasonable confidence which surfaces will afford to the pressure-sensitive adhesive closure high peel resistance both at low and high speeds while not encountering excessively shocky peel at high speeds. The photomicrographs also permit reasonably reliable prediction of when a polyolefin surface might be so rough that the peel resistance might be so high that it might be overly difficult for some users to peel back the adhesive closure.

Of microtopographical measurements that have been made, those obtained using the "Perthometer" profilometer, when equipped with a stylus 5 μm in radius, have proven to be the most meaningful. Measurements with this instrument indicate that the surface of the polyolefin layer at the fastening area should have $R_a$ of from 0.5 to 6 μm
$S_m$ of from 50 to 200 μm
$L_o$ of from 1.01 to 1.15
S of from 60 to 400/cm wherein $R_a$=arithmetical mean deviation of the profile $S_m$=mean spacing of the profile irregularities
$L_o$=relative length of the profile
S=no. of peaks per cm that exceed 0.1 μm in height.

Polyolefin surfaces which satisfy each of these microtopographical measurements do not necessarily afford smooth peelability at high speeds when the above-described class of pressure-sensitive adhesive tapes is used for the fastening tape.

The AB block copolymer of the pressure-sensitive adhesive closure of the invention can have any of a variety of configurations including linear triblock, star, radial, branched, and tapered geometries. The A block is rigid at the service temperature and preferably is styrene or alpha-methylstyrene. The B block is flexible at the service temperature and preferably is either a homopolymer of isoprene or butadiene or a copolymer of ethylene and butylene. The rigid A block usually is present in the range of 8% to 30% by weight of the total block copolymer when the B block is isoprene-based and 20% to 50% by weight when the B block is butadiene-based.

Preferred AB block copolymers include ABA linear triblock copolymers of styrene and isoprene ranging from 10% to about 21% styrene by weight such as those commercially available from Shell Chemical Company as "Kraton" 1107 and 1111 or from Nippon-Zeon as "Quintac" 3420, 3430, and 3530. Also preferred are ABA block copolymers of styrene and butadiene ranging from 25% to 40% styrene by weight such as those commercially available from Firestone Synthetic Latex and Rubber Company as "Stereon" 840A and 845A.

The Tg of the B phase of the blend of AB block copolymer and tackifying resin is calculated from the Fox Equation using the Tg of each component, namely, the Tg of the B block of the block copolymer and the Tg of each tackifying resin in the blend. The Fox equation is $$1/\text{composite } Tg = \Sigma W_i/Tg_i$$

wherein $W_i$ is the weight fraction of each component i and $Tg_i$ is the glass transition temperature of each component i. To enhance the attainment of a composite Tg within the aforementioned range, it is desirable to employ both a liquid and a solid tackifier, even though this can be accomplished with a single semisolid tackifier.

Figure 19:
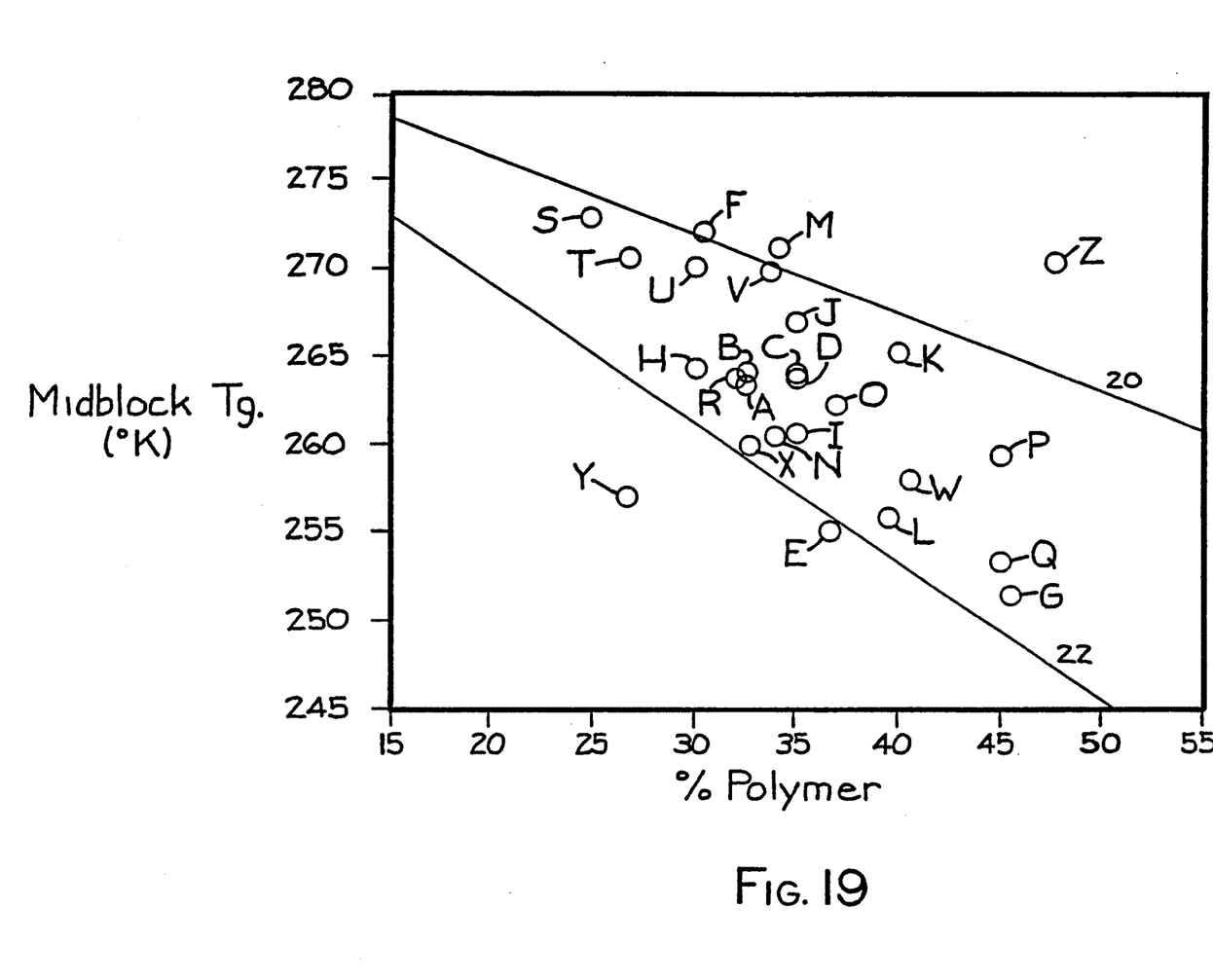
FIG. 19 is a diagram indicating key features of pressure-sensitive adhesives which have been used in diaper closures, some of which have achieved objectives of the invention and some of which have not.

As has been pointed out, the B phase of the blend of AB copolymer and tackifying resin should have a composite Tg between 250° and 275° K., preferably from 258° to 267° K. When the AB block copolymer is a styrene-isoprene-styrene triblock copolymer, the preferred range of composite Tg is indicated by FIG. 19 of the drawing as discussed below.

In preferred pressure-sensitive adhesive closures of the invention, the proportion by weight of the AB block copolymer is from 25 to 50%, more preferably from 30 to 40%; of solid tackifying resin is from 20 to 60%, more preferably from 30 to 50%; and of liquid tackifying resin is from 5 to 45%, more preferably from 10 to 30%.

Useful solid tackifying resins belong to several of the commercially important resin classes including rosin esters; hydrogenated rosin esters; polyterpene resins; polymerized hydrocarbon resins based on piperylene, isoprene, and other conjugated dienes containing 4 to 6 carbon atoms as well as hydrogenated versions of these materials; resins from polymerized and hydrogenated C9 hydrocarbon streams; resins from polymerized and hydrogenated cyclic dienes such as cyclopentadiene; resins from polymerized and hydrogenated pure monomer species such as styrene, vinyl toluene, alphamethyl styrene. Preferred solid tackifying resins include a hydrocarbon resin consisting essentially of polymerized structures derived primarily from a stream of aliphatic petroleum derivatives, both dienes and mono-olefins, containing 4 to 6 carbon atoms. Piperylene and isoprene are the most common species. Such resins are commercially available from Exxon Chemical Company as "Escorez" 1310 and from the Goodyear Chemical Company as "Wingtack Plus" and "Wingtack" 95. Other preferred solid tackifying resins include predominantly cyclopentadiene species that have been polymerized and hydrogenated. Such solid tackifying resins are available from Exxon Chemical Company as "Escorez" 5380, "Escorez" 5300, and "Escorez" 5320. A preferred solid tackifying resin is produced from the polymerization and hydrogenation of a pure monomer feedstock comprising styrene, vinyl toluene, and alpha-methylstyrene, such as "Regalrez" 1094, "Regalrez" 1126 and "Regalrez" 6108 resins available from Hercules Chemical Company. An additional preferred hydrogenated hydrocarbon solid resin is Arkon P-90 available from Arakawa Chemical, USA. Another preferred solid tackifying resin is a partially hydrogenated rosin ester, such as "Permalyn" 1105 available from Hercules Chemical Company. An additional preferred rosin ester is "Permalyn" 305N. A preferred solid tackifying resin for styrene/butadiene block copolymers is a polymerized alpha-pinene resin having a softening point of about 100° C. available from Arizona Chemical Company as "Zonarez" A-100. A second preferred solid tackifying resin for styrene/butadiene block copolymers is a styrenated terpene type resin available as "Wingtack" 86.

Useful liquid tackifying resins include liquid hydrocarbon resins and hydrogenated hydrocarbon resins, liquid polystyrenes, liquid rosin esters, liquid polyterpenes, liquid resins from polymerized and hydrogenated C9 hydrocarbon streams; liquid resins from polymerization and hydrogenation of a cyclic diene such as dicyclopentadiene; liquid resins from polymerized and hydrogenated pure monomer species such as styrene, vinyl toluene, alphamethyl styrene; oils such as naphthenic oils and parafinic oils. Preferred liquid tackifying resins include a liquid hydrocarbon resin consisting essentially of polymerized structures derived primarily from a stream of aliphatic petroleum derivatives, both dienes and mono-olefins, containing 4 to 6 carbon atoms. One such resin is "Wingtack" 10. Another class of liquid tackifying resins can be produced from mixtures of aliphatic and aromatic monomers as exemplified by "Escorez" 2520. Such resins may be further hydrogenated. Another preferred liquid tackifying resin comprises predominantly cyclic dienes that have been polymerized and hydrogenated, e.g., ECR-327 from Exxon Chemical Co. Another preferred liquid tackifying resin is produced from the polymerization and hydrogenation of a pure monomer feedstock comprising styrene, vinyl toluene, and alphamethyl styrene, such as "Regalrez" 1018. Another preferred liquid tackifying resin is a polymerized alpha-pinene resin having a softening point around 25° C. available as "Zonarez" A-25. "Zonarez" A-25 is especially preferred for formulations containing styrene/butadiene block copolymers.

Semisolid tackifying resins suitable for use in this invention include a resin produced from the polymerization and hydrogenation of a pure monomer feedstock comprising styrene, vinyl toluene, and alpha-methylstyrene, e.g., "Regalrez" 1065. Another preferred semisolid tackifying resin is a rosin ester available form Hercules as "Foral" 65.

Conventional additives and fillers may be used in the pressure-sensitive adhesive formulations, including antioxidants such as 2,5-di(tertiary amyl)hydroquinone and t-butylcresol, heat stabilizers such as zinc alkyl dithiocarbamates, ultraviolet stabilizers, pigments, and coloring agents such as zinc oxide, titanium dioxide, carbon black, clay, and calcium carbonate.

Twenty-six pressure sensitive adhesive tapes which have been tested for use in the invention are described below. Two of these, Tapes E and Y, did not exhibit acceptable Shear Adhesion Values although they did exhibit usefully high peel resistance at both low and high speeds. Three others, Tapes F, M, and Z, did not exhibit an acceptably smooth peel at high speeds, although they did exhibit acceptable Shear Adhesion Values. All of the other tapes satisfy the requirements for use in pressure-sensitive adhesive closures of this invention.

PRESSURE-SENSITIVE ADHESIVE TAPE A

A 4-mil (0.1-mm) polypropylene film with a matte surface on both sides was knife-coated with a solution of a pressure-sensitive adhesive. The adhesive solution comprised 35 parts of a styrene-isoprene-styrene (ABA) block copolymer ("Kraton" 1107 from Shell Chemical Co.), 49 parts of a solid hydrocarbon tackifying resin ("Wingtack Plus"), 15 parts of a liquid hydrocarbon tackifying resin ("Wingtack" 10), and 1 part of an antioxidant ("Irganox" 1076 from Ciba Geigy Co.). The solution was 50% solids in 4:1 toluene:heptane. The coating was dried at 70° C. for 5 minutes to result in an adhesive coating weight of 35 g/m$^2$.

PRESSURE-SENSITIVE ADHESIVE TAPES B-U AND Z

Each of Pressure-sensitive Adhesive Tapes B-U and Z was prepared in the same manner as was Pressure-sensitive Adhesive Tape A except as indicated in Table I.

PRESSURE-SENSITIVE ADHESIVE TAPE V-Y

Each of Pressure-sensitive Adhesive Tapes V-Y were prepared by hot melt coating the adhesive onto a 4-mil (0.1 mm) polypropylene film with a matte surface on both sides. This coating was achieved using typical co-rotating twin screw extrusion equipment, specifically, a Werner Pfleiderer model number ZSK-30, as available from Werner Pfleiderer Company, Ramsey, N.J. The block copolymer was fed at the back of the barrel, and the premelted tackifying resins were introduced into the barrel via injection ports along the length of the barrel. The temperature of the molten adhesive was about 310° F. (155° C.) as it exited the coating die.

TESTING

To evaluate the performance of pressure-sensitive adhesive closures, the following tests were made:
Mean Peel Force "Mean Peel Force" was tested using a MTS Model 810 high speed tensile tester in accordance with ASTM D1876-76 except as follows. Each pressure-sensitive adhesive tape sample was one inch (2.54 cm) by 8 inches (20.32 cm), and was laminated by its adhesive layer to the face of a test sample of polyolefin film [2.5 inches (6.35 cm) by 8 inches (20.32 cm)] using two passes of a 4.5-pound (2.04 kg) mechanical roller (at 30 cm/min.) conforming to Federal Standard 147. The whole was then inserted into the jaws of the tensile tester along with a steel panel [2 inches (5.08 cm) by 5 inches (12.7 cm) and 0.0625 inch (0.159 cm) in thickness], against which the polyolefin film rested in order to keep it aligned with the direction of movement of the jaws.

TABLE I

Formulations of each of Tapes A-Z are given in Table I together with their dried coating weights and the composite Tg of the B or midblock phase of the blend of the ABA copolymer and tackifying resin as calculated in the Fox equation. Table I also reports testing for Mean Peel Force (average of 2 tests) and Shear Adhesion Values (average of 5 tests) using Polyolefin Film 1 (described below) as the polyolefin film.

TABLE I

|  | Tg[1] | A | B | C | D | E | F | G | H | I | J | K | L |
|---|---|---|---|---|---|---|---|---|---|---|---|---|---|
| "Kraton" 1107 | 215 | 32.2 |  | 35.0 | 34.6 | 36.7 | 30.3 | 45.5 | 29.7 | 35.0 | 35.0 | 40.0 | 39.5 |
| "Kraton" 1111 | 215 |  | 32.2 |  |  |  |  |  |  |  |  |  |  |
| "Escorez" 5300 | 323 |  |  |  | 41.6 |  | 52.0 |  | 39.6 | 37.0 | 47.0 |  |  |
| "Escorez" 2520 | 253 |  |  |  | 22.8 |  | 16.7 |  | 29.7 | 27.0 | 17.0 |  |  |
| "Escorez" 5320 | 343 |  |  |  |  |  |  |  |  |  |  |  |  |
| "Wingtack" 10 | 245 |  |  | 15.0 |  | 25.6 |  | 17.8 |  |  |  | 5.0 | 20.0 |
| "Wingtack" Plus | 315 |  |  | 49.0 |  | 36.7 |  | 35.6 |  |  |  | 54.0 | 39.5 |
| "Zonarez" A-25 | 251 | 27.2 | 23.7 |  |  |  |  |  |  |  |  |  |  |
| "Piccolyte" HM-105 | 327 | 39.6 | 43.1 |  |  |  |  |  |  |  |  |  |  |
| "Permalyn" 305 N | 315 |  |  |  |  |  |  |  |  |  |  |  |  |
| "Regalrez" 6108 | 325 |  |  |  |  |  |  |  |  |  |  |  |  |
| "Arkon" P-90 | 309 |  |  |  |  |  |  |  |  |  |  |  |  |
| "Irganox" 1076 |  | 1.0 | 1.0 | 1.0 | 1.0 | 1.0 | 1.0 | 1.0 | 1.0 | 1.0 | 1.0 | 1.0 | 1.0 |
| Coating Weight (g/m$^2$) |  | 33.5 | 33.5 | 33.5 | 33.5 | 33.5 | 33.5 | 33.5 | 33.5 | 33.5 | 33.5 | 41.8 | 25.1 |
| Tg of B Phase (°K.) |  | 264 | 264 | 264 | 264 | 255 | 272 | 252 | 264 | 261 | 267 | 265 | 256 |
| Mean Peel Force (N/m) |  |  |  |  |  |  |  |  |  |  |  |  |  |
| at 30 cm/min. |  | 395 | 448 | 434 | 367 | 282 | 449 | 229 | 224 | 174 | 229 | 496 | 304 |
| at 1250 cm/min. |  | 912 | 723 | 833 | 553 | 717 | 204* | 430 | 456 | 396 | 502 | 652 | 562 |
| Shear Adh. Value |  |  |  | 1500 | 1500 | 51 | 1500 | 286 | 1500 | 1500 | 1500 | 1500 | 520 |

[1]Tg in °K. as reported by supplier
*shocky peel

|  | M | N | O | P | Q | R | S | T | U | V | W | X | Y | Z |
|---|---|---|---|---|---|---|---|---|---|---|---|---|---|---|
| "Kraton" 1107 | 34.0 | 34.0 | 37.0 | 45.0 | 45.0 | 32.0 | 24.75 | 26.8 | 30.0 | 33.7 | 40.6 | 32.7 | 26.7 | 45.5 |
| "Kraton" 1111 |  |  |  |  |  |  |  |  |  |  |  |  |  |  |
| "Escorez" 5300 |  |  |  | 42.0 | 32.0 | 40.0 | 49.5 | 47.5 | 49.0 |  |  |  |  |  |
| "Escorez" 2520 |  |  |  | 12.0 | 22.0 | 27.0 | 24.8 | 24.7 | 20.0 | 14.9 | 21.8 | 24.8 | 41.6 | 4.5 |
| "Escorez" 5320 |  |  |  |  |  |  |  |  |  |  |  |  |  | 49.0 |
| "Wingtack" 10 | 5.0 | 22.0 | 14.0 |  |  |  |  |  |  |  |  |  |  |  |
| "Wingtack" Plus | 60.0 | 43.0 | 48.0 |  |  |  |  |  |  |  |  |  |  |  |
| "Zonarez" A-25 |  |  |  |  |  |  |  |  |  |  |  |  |  |  |
| "Piccolyte" HM-105 |  |  |  |  |  |  |  |  |  |  |  |  |  |  |
| "Permalyn" 305 N |  |  |  |  |  |  |  |  |  |  |  |  |  |  |
| "Regalrez" 6108 |  |  |  |  |  |  |  |  |  | 50.5 | 36.6 |  |  |  |
| "Arkon" P-90 |  |  |  |  |  |  |  |  |  |  |  | 41.6 | 30.7 |  |
| "Irganox" 1076 | 1.0 | 1.0 | 1.0 | 1.0 | 1.0 | 1.0 | 1.0 | 1.0 | 1.0 | 1.0 | 1.0 | 1.0 | 1.0 | 1.0 |
| Coating Weight (g/m$^2$) | 25.1 | 41.8 | 33.5 | 41.8 | 41.8 | 33.5 | 33.5 | 33.5 | 33.5 | 33.5 | 33.5 | 33.5 | 33.5 | 25.1 |
| Tg of B Phase | 271 | 260 | 262 | 259 | 253 | 264 | 273 | 271 | 270 | 270 | 258 | 260 | 257 | 270 |
| Mean Peel Force (N/m) |  |  |  |  |  |  |  |  |  |  |  |  |  |  |
| at 30 cm/min. | 391 | 421 | 401 | 312 | 269 | 386 | 552 | 510 | 476 | 579 | 396 | 331 | 278 | 525 |
| at 1250 cm/min. | 271* | 807 | 743 | 655 | 567 | 845 | 549 | 979 | 526 | ** | 859 | 820 | 880 | 185* |
| Shear Adh. Value | 1500 | 1500 | 1500 | 1500 | 1500 | 1500 | 1152 | 1210 | 1500 | 1500 | 680 | 469 | 106 | 1500 |

[1]Tg as reported by supplier
*indicates shocky peel
**indicates tape tear

Shear Adhesion Value

"Shear Adhesion Value" was tested by PSTC-7 except as follows. A polyolefin film was reinforced by laminating to the non-test surface of the film the adhesive layer of a pressure-sensitive adhesive tape having a 0.089 mm thick polypropylene backing (Y-8450 from Minnesota Mining and Manufacturing Company). A fastening tape then was laminated by its adhesive layer to the test surface of the polyolefin film [1 inch by 1 inch (2.54 by 2.54 cm) test area]. After being allowed to dwell for 15 minutes in an air-circulating oven at 100° F. (38° C.), the bond to the polyolefin film was tested with a 1000-gram weight attached immediately. The time to fail was recorded, and the test was discontinued if no failure occurred within 1500 minutes.

THE DRAWING

The invention may be better understood in connection with the drawing in which.

Figure 17:
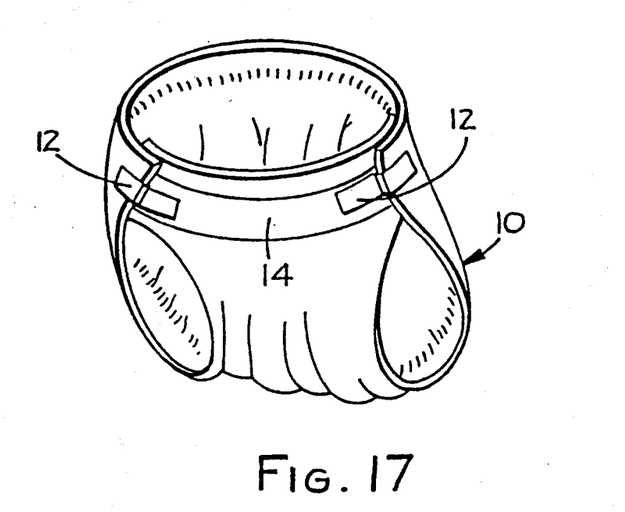
FIG. 17 is a perspective view of a diaper incorporating a pressure-sensitive adhesive closure of the invention.
Figure 18:
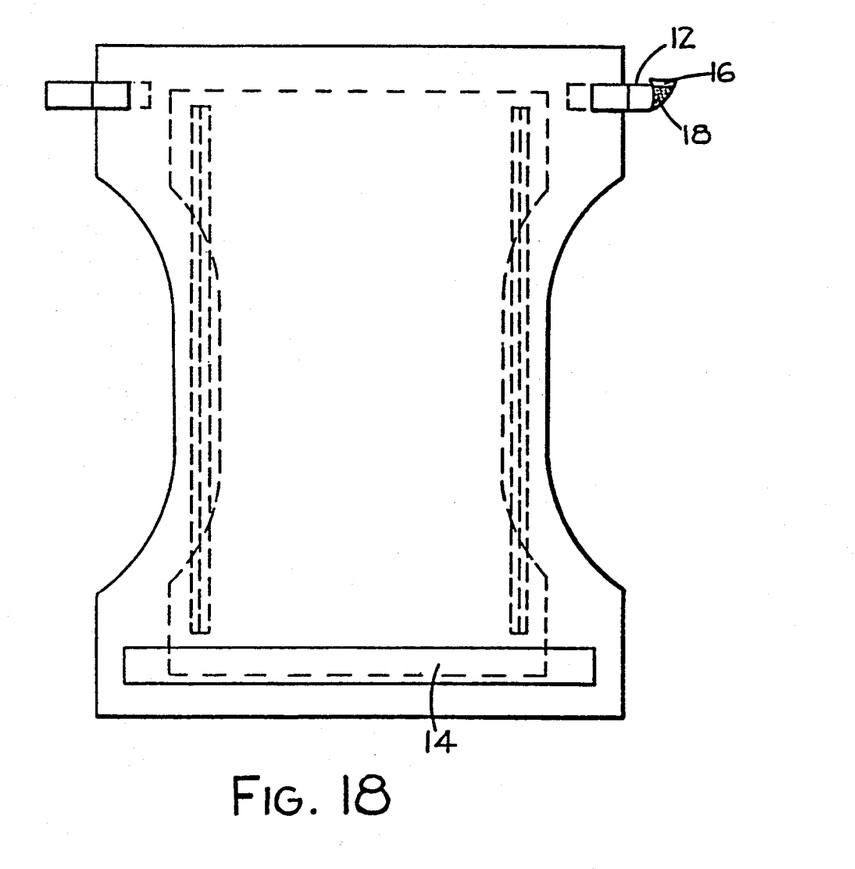
FIG. 18 shows the diaper of FIG. 17 laid flat.

Referring first to FIGS. 17 and 18, a diaper 10 has a pressure-sensitive adhesive closure consisting of a pressure-sensitive adhesive tape 12 and a rectangle 14 of polyolefin film covering the fastening area of the diaper. The end of the tape has been folded over to provide a narrow nonadhesive tab 16 while leaving a pressure-sensitive adhesive area 18. The diaper can be opened and either discarded, or the closure can be refastened by pressing the adhesive-bearing area 18 of the tape against the rectangle 14.

FIG. 19 of the drawing shows key characteristics of each of the adhesive blends of each of Pressure-sensitive Adhesive Tapes A-Z. Those blends having characteristics between lines 20 and 22 of FIG. 19, when tested with Polyolefin Film 1 (as reported in Table I, above), afforded the objectives of the invention while the other blends did not. As indicated in Table I, Tapes E and Y (below line 22) were deficient in Shear Adhesion Values; and Tapes, F, M and Z (above line 20) exhibited excessively shocky peel at high speeds. Tapes close to either of lines 20 or 22 generally provided marginal performance, while optimum results generally were attained midway between the lines, e.g., by Tapes A, B, C, P, and W.

When the pressure-sensitive adhesive is a styrene-butadiene-styrene (ABA) triblock copolymer, each of the lines 20 and 22 would be lowered about 5°–10° K. in order to encompass formulations that would afford the objectives of the invention. Substitution of other polyolefin films for Polyolefin Film 1 may also result in a shift in the lines 20 and 22. Differences in adhesive coating thickness can also affect performance as is well known in the art.

A large number of polyolefin films have been tested for use in the invention. Illustrative of polyolefin films which have been tested include Polyolefin Films 1–6, each of which has provided the objectives of the invention, and Polyolefin Films 7–12, which have not. In describing these polyolefin films, all parts are given by weight.

POLYOLEFIN FILM 1

A polypropylene resin (PP-3085B from Exxon Chemical Corp.) with a melt index of 35 g/10 minutes was extruded at a temperature of 260° C. through a slot extrusion die using a typical single-screw extruder. The melt exiting the die was passed into a nip between a metal roll covered with "Teflon" (polytetrafluoroethylene) and a water-cooled metal chill roll (water temperature, 18° C.) to result in a film with a basis weight of 44 g/m$^2$ and a caliper of 56 $\mu$m. Both the chill roll and the "Teflon"-covered roll had microtopographical features, the negative images of which were replicated in the polypropylene polymer film. The face of the film which contacted the metal chill roll is here called "Polyolefin Film 1" and is shown in FIG. 1 of the drawing.

Figure 1:
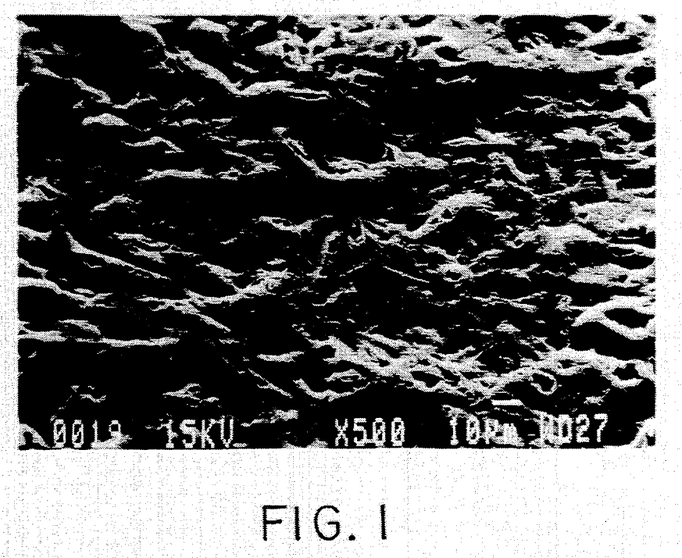
FIGS. 1–12 are photomicrographs at 500× of surfaces of the below-described Polyolefin Films 1–12, respectively, of which Polyolefin Films 1–6 can be used to cover the fastening areas of a diaper in a pressure-sensitive adhesive closure of the invention whereas the objectives of the invention have not been achieved when using polyolefin Films 7–12.

The FIG. 1 face of Polyolefin Film 1 has a large number of closely spaced asperities at least two micrometers in height that have a jagged appearance at 500×. Between these asperities are a few isolated, relatively smooth areas. The asperities appear to be in the form of steep hills or peaks having an average height of about 8–10 $\mu$m, with the average distance between adjacent peaks being about 10 $\mu$m. At the crowns of most of the peaks are what appear to be craters having sharp edges. The average distance between adjacent peaks is approximately the same in every direction.

Figure 14:
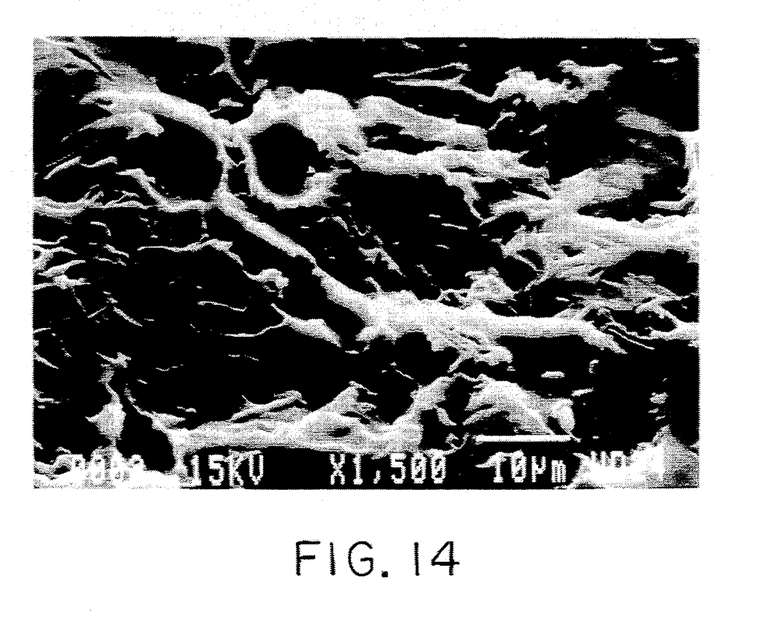

By viewing Polyolefin Film 1 at 1500× as in FIG. 14, the nature of the individual steep hills can be better appreciated.

POLYOLEFIN FILM 2

A polypropylene resin as described in making Polyolefin Film 1 was extruded in the same manner except using a different metal chill roll and a metal roll covered with a silicone rubber coating instead of "Teflon." The resulting film had the same basis weight and caliper as did Polyolefin Film 1. The face of the film which contacted the silicone-covered roll is here called "Polyolefin Film 2" and is shown in FIG. 2 of the drawing.

Figure 2:
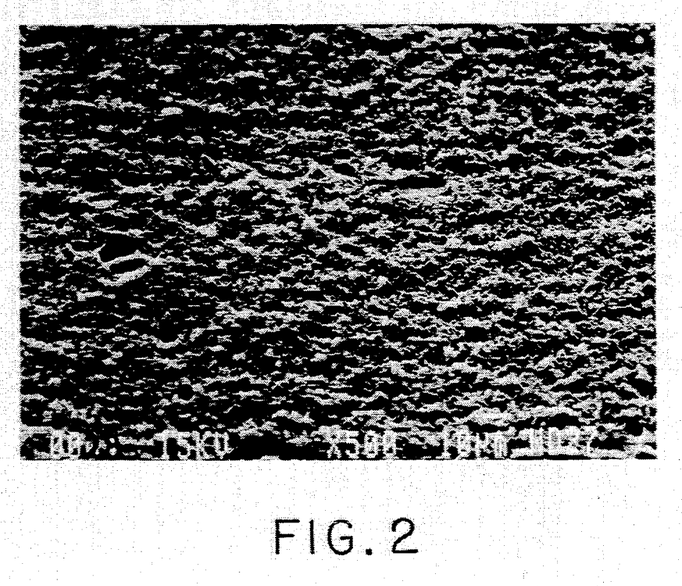
Figure 13:
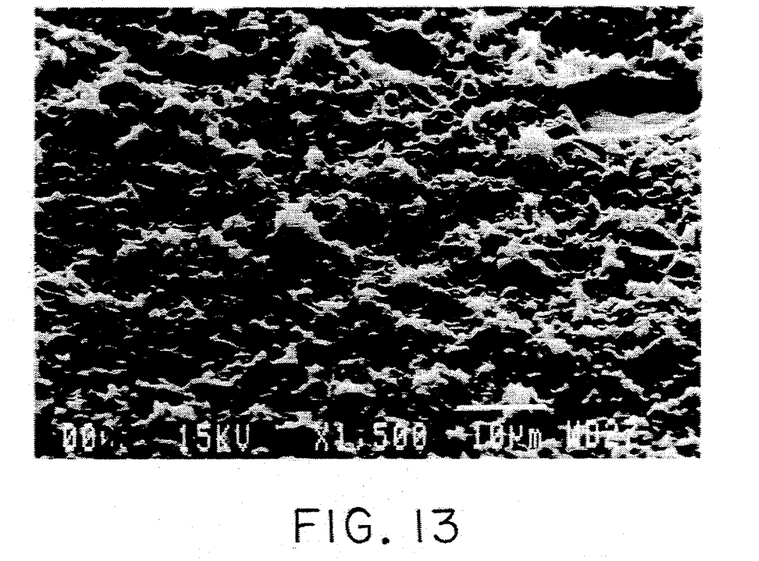
FIGS. 13, 14 and 15 are photomicrographs at 1500× of Polyolefin Films 2, 1 and 7, respectively.

The FIG. 2 face of the Polyolefin Film 2 has at 500× a large number of closely spaced asperities that have a jagged appearance covering virtually 100% of its area. The asperities appear to be in the form of craggy peaks having an average height of about 2 $\mu$m, with the average distance between adjacent peaks being about 2 $\mu$m. The average distance between adjacent peaks is approximately the same in every direction. The true nature of these peaks can be better appreciated at 1500× as seen in FIG. 13 of the drawing.

This Polyolefin Film 2 provides such high peel values that some users would be likely to complain that pressure-sensitive adhesive closures of the invention are too difficult to open if this film were to be used. Accordingly, it is suggested that surfaces rougher than the FIG. 2 face of Polyolefin Film 2 should be avoided in diaper closures of the invention.

POLYOLEFIN FILM 3

Figure 3:
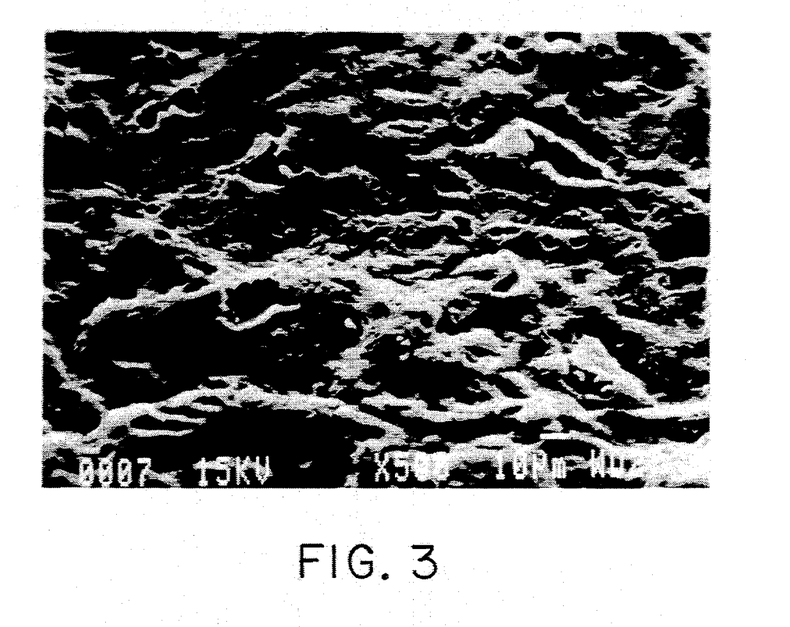

Polyolefin Film 3 was prepared in the same manner as Polyolefin Film 1 except using a different chill roll. The description given above for Polyolefin Film 1 generally applies to Polyolefin Film 3, as seen in FIG. 3, except that the average distance between adjacent peaks appears to be about 12–15 $\mu$m.

POLYOLEFIN FILM 4

Figure 4:
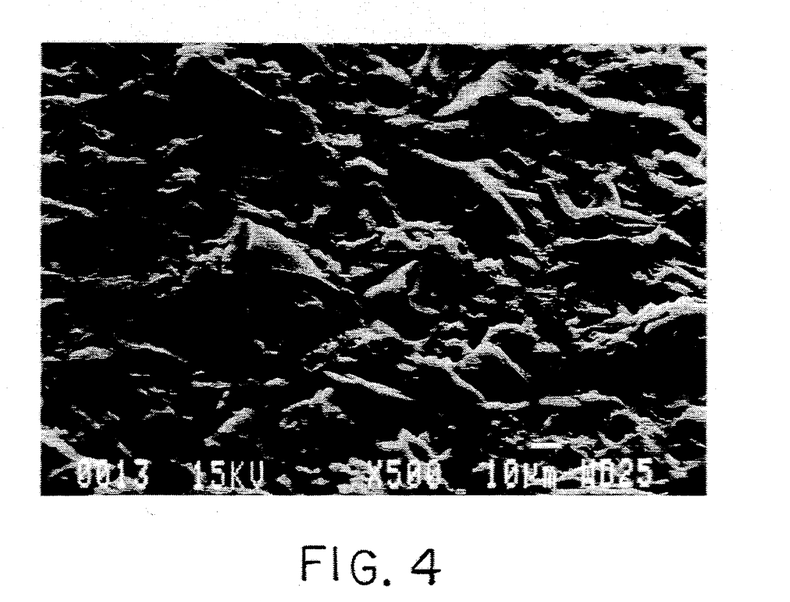

FIG. 4 shows the matte face of a polypropylene film 3.0 mils (75 $\mu$m) in thickness obtained as "Extrel" 30 from Exxon Chemical Film Division, Pottsville, Pa. The FIG. 4 face of the Polyolefin Film 4 is rather similar to the faces of Polyolefin Films 1 and 3 except that its individual asperities, while likewise being generally nondescript, are somewhat larger and no craters are evident. The face of Polyolefin Film 4 appears to have a few smooth areas exceeding 100 $\mu$m:, so that the asperities which have a jagged appearance cover only about 90% of the area.

POLYOLEFIN FILM 5

Figure 5:
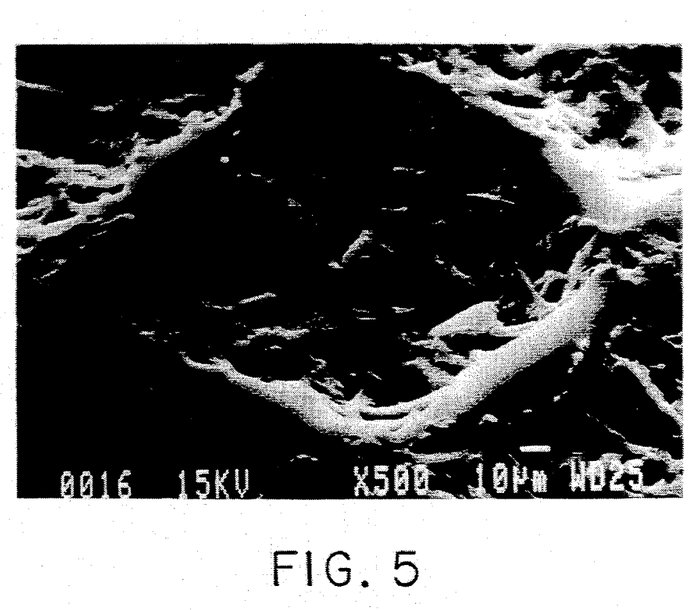

FIG. 5 shows the embossed face of a polypropylene film 2.5 mils (63 $\mu$m) in thickness which had been embossed in a diamond pattern, as can be seen in FIG. 5. Although Polyolefin Film 5 has a smooth area at each ridge of the diamond pattern and each smooth area substantially exceeds 100 $\mu$m$^2$ in area, the surface asperities covering about 85% of the total area of Polyolefin Film 5 have a jagged appearance that indicates utility in the present invention. Like the surface asperities of Polyolefin Films 1, 3 and 4, those of Polyolefin Film 5 are of generally nondescript appearance. They appear to average about 8–10 μm in height, and the average distance between the peaks of the asperities appears to be about 10–20 μm.

POLYOLEFIN FILM 6

Figure 6:
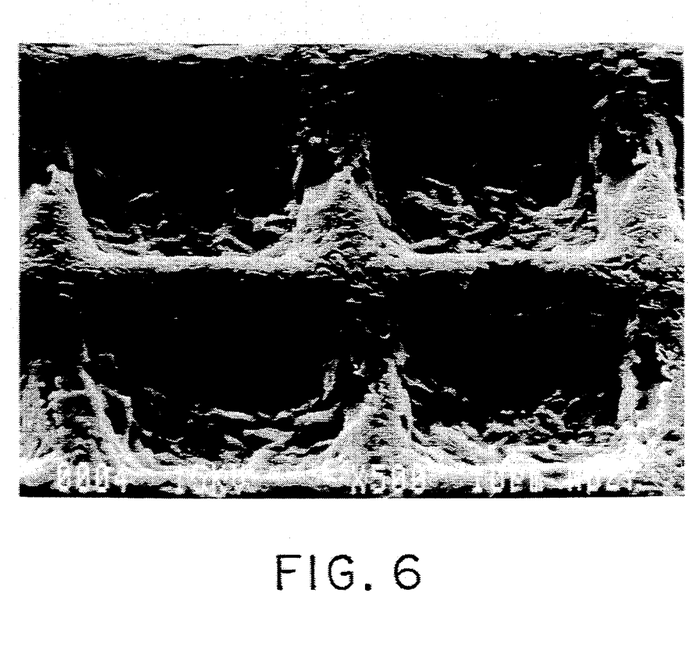

FIG. 6 shows the embossed face of a polypropylene film 2.0 mils (50 μm) in thickness, obtained as "Microflex" Embossed Code XII from Clopay Corporation. It had been embossed in a pattern similar to that of Polyolefin Film 5 except the embossed ridges extend to a greater height. The surface asperities of Polyolefin Film 6 appear to be somewhat smaller than those of Polyolefin Film 5, rising to what appears to be an average height of about 4–6 μm. Nevertheless, the asperities of Polyolefin Film 6 provide a jagged appearance at 500× covering about 70% of the total area, thus indicating that the FIG. 6 face of Polyolefin Film 6 should be useful for covering the fastening area of a diaper of the present invention. The average distance between adjacent peaks of the individual asperities appears to be about 5–10 μm, and the average distance between adjacent peaks is approximately the same in every direction.

POLYOLEFIN FILM 7

Figure 7:
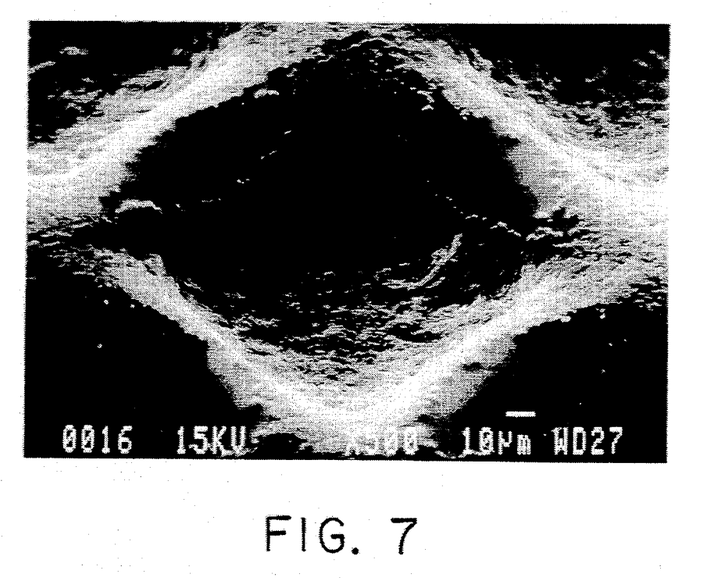
Figure 15:
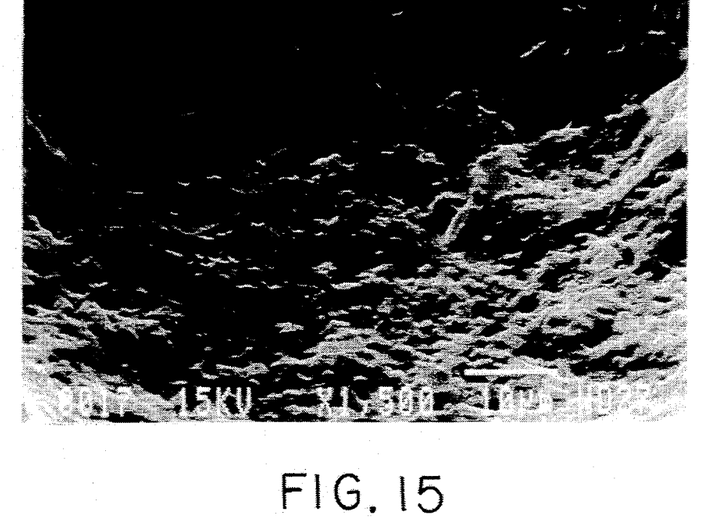

FIG. 7 shows the embossed face of a polypropylene film 2.0 mil (50 μm) in thickness obtained as "4301A" from Edison Plastics Company. It had been embossed in the same manner as were Polyolefin Films 5 and 6. The smooth areas at the tops of the ridges of the embossed pattern appear to cover approximately 25% of the total area. The surface asperities in the other areas have a jagged appearance at 500×, but when viewed in FIG. 15 at 1500×, it becomes more evident that individual asperities have an average height of only about 1 μm and appear to be more flat than jagged. The FIG. 7 face of Polyolefin Film 7 has not afforded the properties desired in pressure-sensitive adhesive closures of the invention.

POLYOLEFIN FILM 8

Figure 8:
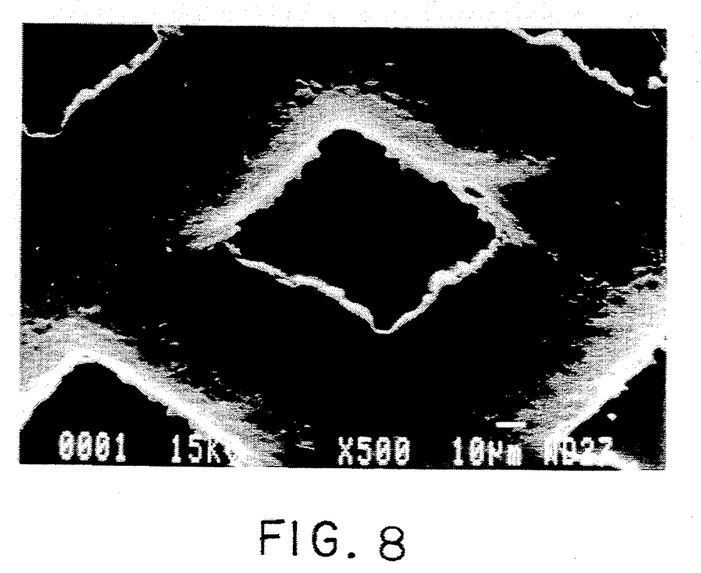

FIG. 8 shows the embossed face of a polypropylene film 2.0 mil (50 μm) in thickness obtained as "EM-65R" from Consolidated Thermoplastics Company. It had been embossed with a pattern similar to those of Polyolefin Films 5, 6 and 7. At 500×, the surface asperities of Polyolefin Film 8 have a generally rounded appearance except at the edges of the embossing pattern. The FIG. 8 face of Polyolefin Film 8 has not afforded the properties desired in pressure-sensitive adhesive closures of the invention.

POLYOLEFIN FILM 9

Figure 9:
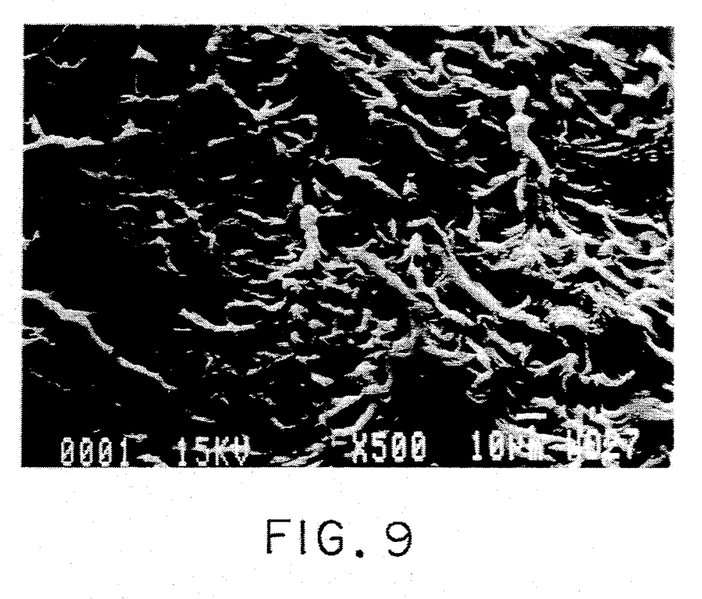
Figure 16:
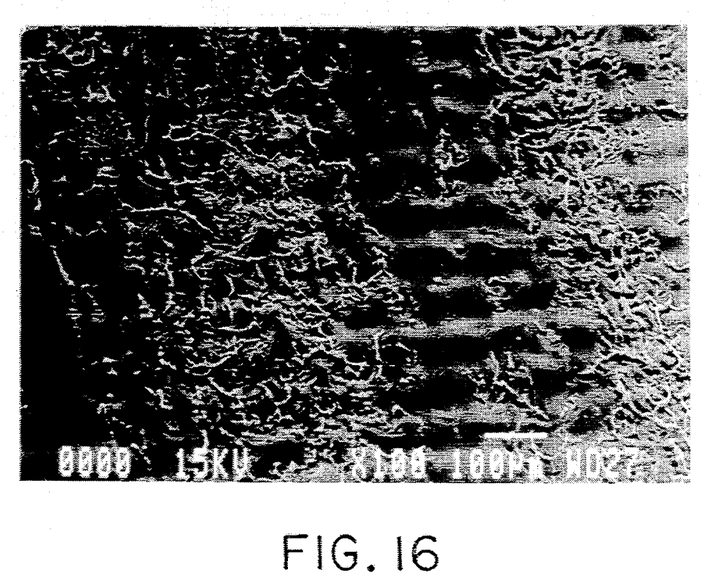
FIG. 16 is a photomicrograph at 100× of Polyolefin Film 9.

FIG. 9 shows the obverse surface of Polyolefin Film 6, which obverse surface appears to have a large number of surface asperities (ridges) that have a jagged appearance at 500× and are more than 2 micrometers in height. Although these surface asperities appear to cover somewhat more than half of the total area of FIG. 9, it can be seen from FIG. 16 at 100× that large areas of the surface are rather smooth and that the 500× magnification of FIG. 9 shows only a relatively rough portion of the total surface. From viewing both FIGS. 9 and 16, it can be seen that more than half of the total surface would have a smooth or rounded appearance at 500×. The FIG. 9 face of Polyolefin Film 9 has not afforded the properties desired in pressure-sensitive adhesive closures of the invention, but it is believed that it might have afforded the desired properties if its FIG. 9 were representative of its overall appearance at 500×.

POLYOLEFIN FILM 10

Figure 10:
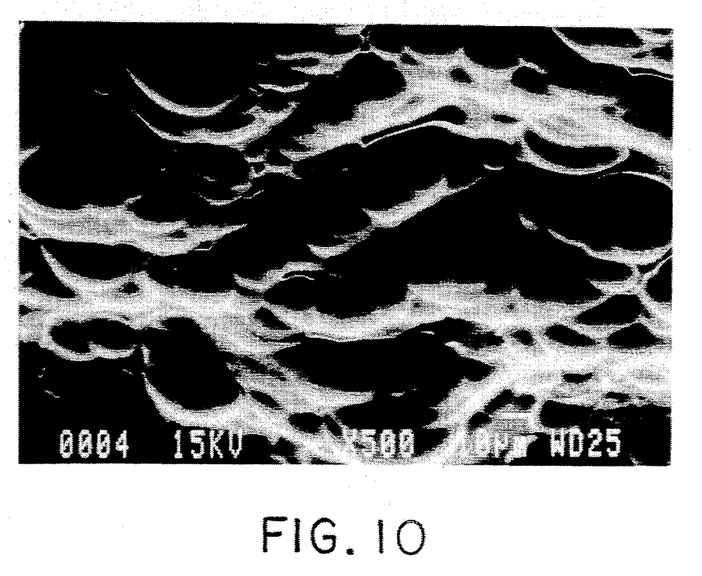

FIG. 10 shows the matte face of a polypropylene film 2.5 mils (63 μm) in thickness obtained as "Extrel" 31 from Exxon Chemical Americas Film Division. Its surface asperities appear to be rounded depressions, a few of which appear to be greater than 10 μm in depth. The FIG. 10 face of Polyolefin Film 10 has not afforded properties desired in the present invention.

POLYOLEFIN FILM 11

Figure 11:
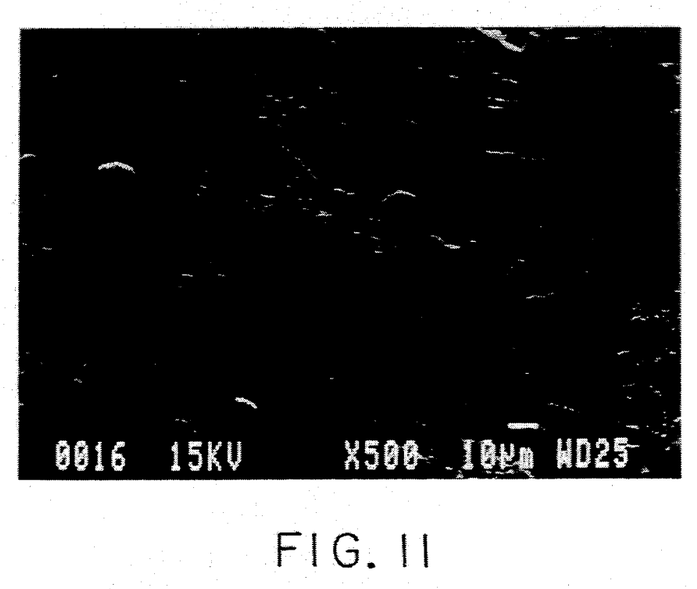

FIG. 11 shows the obverse face of the film called "Polyolefin Film 4". "Polyolefin Film 11" has a generally smooth surface with some rounded ridges and valleys. The average height (and depth) of these ridges (and valleys) appears to be less than 1 μm. The FIG. 11 face of Polyolefin Film 11 has not afforded properties desired in the present invention.

POLYOLEFIN FILM 12

Figure 12:
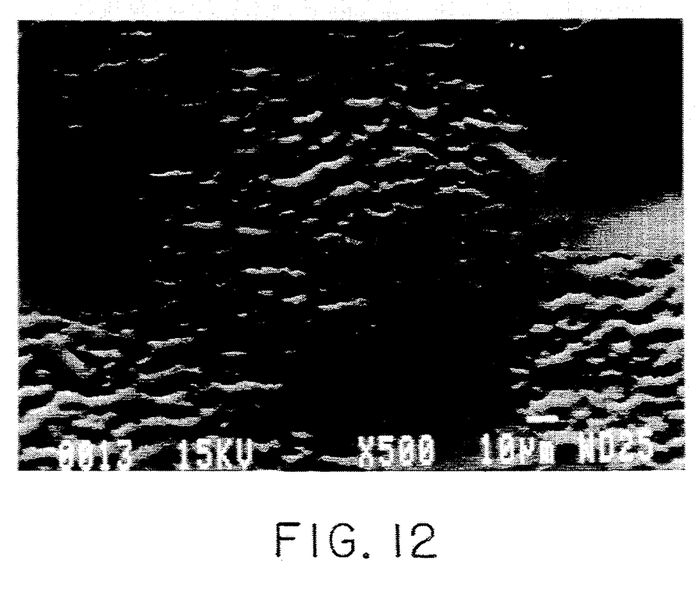

FIG. 12 shows the obverse face of Polyolefin Film 5. At 500× its surface asperities appear to be rounded. The FIG. 12 face of Polyolefin Film 12 has not afforded properties desired in pressure-sensitive adhesive closures of the present invention.

Reported in Table II are microtopographical measurements of Polyolefin Films 1–12 obtained using the above-cited "Perthometer" profilometer.

TABLE II

| Polyolefin Film | Ra (μm) | Sm (μm) | $L_o$ | S (cm$^{-1}$) |
| --- | --- | --- | --- | --- |
| 1 | 1.78 | 106 | 1.056 | 246 |
| 2 | 0.51 | 69 | 1.015 | 390 |
| 3 | 1.72 | 100 | 1.038 | 195 |
| 4 | 1.42 | 74 | 1.042 | 244 |
| 5 | 5.70 | 177 | 1.059 | 71 |
| 6 | 5.38 | 101 | 1.109 | 103 |
| 7 | 10.62 | 210 | 1.095 | 58 |
| 8 | 4.89 | 188 | 1.047 | 60 |
| 9 | 1.21 | 100 | 1.025 | 206 |
| 10 | 6.42 | 231 | 1.084 | 81 |
| 11 | 1.26 | 69 | 1.041 | 271 |
| 12 | 0.88 | 215 | 1.009 | 198 |

EXAMPLES OF SIMULATED DIAPER CLOSURES

Diaper closures were simulated in testing each of Polyolefin Films 1–12 in combination with Pressure-sensitive Adhesive A, and results are reported in Table III.

TABLE III

| Polyolefin Film | Mean Peel Force (N/m) at 30 cm/min. | Mean Peel Force (N/m) at 1250 cm/min. | Peel Quality* at 1250 cm/min. | Shear Adhesion Value (min.) |
| --- | --- | --- | --- | --- |
| 1 | 435 | 830 | Smooth | 1500+ |
| 2 | 500 | 940 | Smooth | 1500+ |
| 3 | 550 | 1020 | Smooth | 1500+ |
| 4 | 340 | 745 | Smooth | 1500+ |
| 5 | 195 | 560 | Smooth | 1500+ |
| 6 | 220 | 630 | Smooth | 177 |
| 7 | 190 | 245 | Marginal | 150 |
| 8 | 380 | 235 | Shocky | 588 |
| 9 | 350 | 210 | Shocky | 1500+ |
| 10 | 270 | 350 | Marginal | 91 |

TABLE III-continued

| Poly-olefin Film | Mean Peel Force (N/m) at 30 cm/min. | at 1250 cm/min. | Peel Quality* at 1250 cm/min. | Shear Adhesion Value (min.) |
| --- | --- | --- | --- | --- |
| 11 | 320 | 160 | Shocky | 1500+ |
| 12 | 290 | 130 | Shocky | 105 |

*Smooth = Instantaneous peel force substantially within 20% of Mean Peel Force
Shocky = Instantaneous peel force generally not within 20% of Mean Peel Force
Marginal = Somewhat smooth and somewhat shocky

We claim:

1. A diaper comprising an impermeable matte-surfaced outer sheet that covers an inner absorbent layer; adhesive closure tabs attached to corners of the outer sheet; and a matte-surfaced polyolefin film applied onto the outer sheet and covering and reinforcing the fastening area of the diaper to which the closure tabs are adhered in fastening the diaper around a wearer; the closure tabs adhering to the matte surface of the film with a Mean Peel Force of at least 175 N/m at a speed of either 30 centimeters per minute or 1250 centimeters per minute, and the Mean Peel Force at a peel speed of 1250 centimeters per minute being at least 80 percent of the Mean Peel Force at a peel speed of 30 centimeters per minute.

2. A diaper of claim 1 in which the adhesive bond between the closure tabs and the matte surface of the polyolefin film has a Shear Adhesion Value of at least 150 minutes.

3. A diaper of claim 1 in which the matte surface of the polyolefin film has a large number of closely spaced asperities that have a jagged appearance at about 500×, are present over at least one-half the fastening surface, and are at least two micrometers in height.

4. A diaper of claim 3 in which the adhesive of the closure tabs comprises a blend of 1) an AB block copolymer wherein A comprises vinylarene, B comprises a polymer of at least one monomer selected from conjugated dienes and lower alkenes, and A comprises from 8 to 50 weight percent of the block copolymer, and 2) tackifying resin, the AB copolymer comprising from 20 to 60 weight percent of total AB copolymer plus tackifier and the B phase of the blend have a composite Tg of from 250° to 275° K.

5. Diaper of claim 3 in which the matte surface of the polyolefin film has, by measurement with a "Perthometer" profilometer equipped with a stylus 5 μm in radius, a $R_a$ of from 0.5 to 6 μm
$S_m$ of from 50 to 200 μm
$L_o$ of from 1.01 to 1.15
S of from 60 to 400/cm wherein
$R_a$ = arithmetical mean deviation of the profile
$S_m$ = mean spacing of the profile irregularities
$L_o$ = relative length of the profile
S = number of peaks per cm that exceed 0.1 μm in height.

* * * * *